US007053383B2

(12) United States Patent
Moore

(10) Patent No.: US 7,053,383 B2
(45) Date of Patent: May 30, 2006

(54) METHOD AND APPARATUS FOR RAPID SAMPLE PREPARATION IN A FOCUSED ION BEAM MICROSCOPE

(75) Inventor: Thomas M. Moore, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 13 days.

(21) Appl. No.: 10/896,596

(22) Filed: Jul. 22, 2004

(65) Prior Publication Data

US 2006/0016987 A1    Jan. 26, 2006

Related U.S. Application Data

(60) Provisional application No. 60/519,046, filed on Nov. 11, 2003.

(51) Int. Cl.
*G01F 23/00*    (2006.01)

(52) U.S. Cl. .................................. 250/440.11
(58) Field of Classification Search ............ 250/440.11
See application file for complete search history.

(56) References Cited

U.S. PATENT DOCUMENTS

| 5,270,552 | A  | 12/1993 | Ohnishi et al. |
| 6,080,991 | A  | 6/2000  | Tsai |
| 6,300,631 | B1 | 10/2001 | Shofner |
| 6,523,239 | B1 * | 2/2003 | Peterson et al. ....... 29/243.517 |
| 6,664,552 | B1 | 12/2003 | Shichi et al. |
| 6,714,289 | B1 | 3/2004 | Haraguchi |
| 6,717,156 | B1 | 4/2004 | Sugaya et al. |
| 2002/0000522 | A1 | 1/2002 | Alani |
| 2003/0150836 | A1 | 8/2003 | Tsung et al. |
| 2004/0004186 | A1 | 1/2004 | Jiyan et al. |
| 2004/0016880 | A1 | 1/2004 | Reiner et al. |
| 2004/0178355 | A1 * | 9/2004 | Rasmussen ............ 250/442.11 |

OTHER PUBLICATIONS

Altmann, F., FIB-Pinpointed Preparation of TEM Samples by a Needle Based Manipulator (Lift-Out) Technique, Practical Metallography, 2003, pp. 175-183, vol. 40, No. 4.
Anderson, R., Comparison of FIB TEM Specimen Preparation Methods, Microscopy and Microanalysis, 2002, p. 44, vol. 8, Suppl. 2.

(Continued)

*Primary Examiner*—Nikita Wells
*Assistant Examiner*—Jennifer Yantomo
(74) *Attorney, Agent, or Firm*—John A. Thomas

(57) ABSTRACT

A coupon for preparing a TEM sample holder comprises a sheet of material that includes a TEM sample holder form. There is at least one section of the sheet connecting the TEM sample holder form to other portions of the sheet. A TEM sample holder is formed by cutting the TEM sample holder form from the coupon in a press. The cutting joins the tip point of a nano-manipulator probe tip with the formed TEM sample holder. The tip point of the probe has a sample attached for inspection in a TEM.

8 Claims, 10 Drawing Sheets

OTHER PUBLICATIONS

Bicais-Lepinay, N.; Andre, F.; Pantel, R.; Jullian, S. Margain, A.; Kwakman, L. F. Tz., Lift-out techniques coupled with advanced TEM characterization methods for electrical.

Burkhardt, C., Nisch, W. , In-Situ Lift-Out of TEM—Samples by Micro Manipulation in a Scanning Electron Microscope ,Practical Metallography, 2004, pp. 190-198, vol. 41.

Crawford, E. J.; Gignac, L.; Barth, K.; Petrus, J.; Levine, E. , Focused Ion Beam Sectioning and Lift-out Method for Copper and Resist Vias in Organic Low-k Dielectrics., Mic.

Dai, J. Y.; Tee, S. F.; Tay, C. L.; Song, Z. G.; Ansari, S.; Er, E.; Redkar, S. , Development of a rapid and automated TEM sample preparation method in semiconductor failure a.

Engelmann H.-J., Volkmann, B., Zschech, E. , From SEM Cross-Section to TEM Sample—New Capabilities of FIB Sample Preparation by "Refill" Technique, Practical Metallography.

Gnauck, P.; Hoffrogge, P.; Schumann, M.; Bauhammer, G., Enhanced Site specific Preparation of SEM Cross Sections and TEM Samples by using CrossBeam Technology, Microscopy and.

Kempshall, B.W., Schwarz, S.M., Giannuzzi, L.A. , In-situ FIB lift-out for site specific TEM specimen preparation of grain boundaries and interfaces, ICEM 15, 2002, pp. 249-.

Kempshall, B.W and Giannuzzi, L.A., IN-Situ Lift-Out FIB Specimen Preparation for TEM of Magnetic Materials, Microscopy and Microanalysis, 2002, pp. 390-391, vol. 8, Suppl.

Langford, R.M., Petford-Long, A.K. and Gnauck, P. , Focused Ion Beam Based Sample Preparation Techniques, Microscopy & Microanalysis, 2002, pp. 46-47, vol. 8, Suppl. 2, Lee, J.

Chuang, J.H. , A Novel Application of the FIB Lift-out Technique for 3-D TEM Analysis , Microelectronics Reliability, 2001, pp. 1551-1556 , vol. 41.

Mohammad, K. N.; Sim, K. S., Novel Application of FIB Lift-out and Ultramicrotomy for Advanced Package Failure Analysis , Proceedings of the 9th International Symposium on the.

Subramanian, Swaminathan; Rose, Stewart; Conner, James; Schani, Phil; Moss, Jamey , Specific Area Planar and Cross-Sectional Lift-Out Techniques: Procedures and Novel Applicat.

Ritz, Y., Stegmann, H., Engelmann, H.-J., Zschech, E. , Target Preparation of Samples for 3D-TEM Using Micromanipulator, Practical Metallography, 2004, pp. 180-189, vol. 41.

Shofner, T. L.; Drown, J. L.; Brown, S. R.; Rossie, B. B.; Decker, M. A.; Obeng, Y. S.; Stevie, F. A. , Planar TEM Analysis of Nanoindented Samples Using the Focused Ion Beam.

Stevie, F. A.; Irwin, R.B.; Shofner, T. L; Brown, S.R.; Drown, J. L.; Giannuzzi, L.A., Plan View TEM Sample Preparation Using the Focused Ion Beam Lift-Out Technique, CP449.

Veirman De, A. E. M. , '3-Dimensional' TEM silicon-device analysis by combining plan-view and FIB sample preparation , Materials Science & Engineering B , 2003 , pp. 63-69 , v.

Gnauck, P.; Zeile, U.; Hoffrogge, P.; Benner, G.; Orchowski, A.; Rau, W-D., Real time SEM imaging FIB of milling processes for extended accuracy on TEM samples for EFTEM analy.

* cited by examiner

METHOD AND APPARATUS FOR RAPID SAMPLE PREPARATION IN A FOCUSED ION BEAM MICROSCOPE

CLAIM FOR PRIORITY

This patent application claims priority from U.S. provisional patent application No. 60/519,046, filed on Nov. 11, 2003.

BACKGROUND

The use of focused ion-beam (FIB) microscopes has become common for the preparation of specimens for later analysis in the transmission electron microscope (TEM). The structural artifacts, and even some structural layers, in the device region and interconnect stack of current integrated-circuit devices can be too small to be reliably detected with the secondary electron imaging in a Scanning Electron Microscope (SEM), or FIB, which offers a bulk surface imaging resolution of approximately 3 nm. In comparison, TEM inspection offers much finer image resolution (<0.1 nm), but requires electron-transparent (<100 nm thick) sections of the sample mounted on 3 mm diameter grid disks.

Techniques were later developed for cutting out and removing specimens for examination that required little or no preliminary mechanical preparation of the initial semiconductor die sample before preparation in the FIB. These lift-out techniques include an "ex-situ" method that is performed outside the FIB chamber, and "in-situ" methods performed inside the FIB.

The in-situ lift-out technique is a series of FIB milling and sample-translation steps used to produce a site-specific specimen for later observation in a TEM or other analytical instrument. During in-situ lift-out, a sample of material (usually wedge-shaped) containing the region of interest is first completely excised from the bulk sample, such as a semiconductor wafer or die, using ion-beam milling in the FIB. This sample is typically 10×5×5 μm in size. Removal of the lift-out sample is then performed using an internal nano-manipulator in conjunction with the ion-beam assisted chemical vapor deposition (CVD) process available with the FIB tool. A suitable nano-manipulator system is the Omniprobe AutoProbe 200, manufactured by Omniprobe, Inc., of Dallas, Tex. The material deposited in the CVD process is typically a metal or an oxide.

A TEM sample holder is then positioned in the field of view in the FIB, and the nano-manipulator is used to lower the lift-out sample onto the edge of the sample holder. The CVD metal deposition capability inside the FIB vacuum chamber is then used to secure the sample to the TEM sample holder. Once the sample is attached to the TEM sample holder, the probe-tip point is separated from the sample by ion milling. The portion of the method involving the operations that include the TEM sample holder is referred to as the "holder attach" step. The sample may then be milled using conventional FIB milling steps to prepare a thin area for TEM inspection or other analysis. Details on methods of in-situ lift-out may be found in the specifications of U.S. Pat. Nos. 6,420,722 and 6,570,170. These patent specifications are incorporated into this application by reference, but are not admitted to be prior art with respect to the present application by their mention in this background section.

The in-situ lift-out technique has become popular, because this method allows one to both take advantage of the FIB's unique capabilities and to extend these capabilities to the inspection of structures and defects in next-generation devices. Due to the small ion-beam spot size achievable by new FIB instruments (e.g., <10 nm), FIB specimen preparation techniques presently offer the best spatial resolution where site specificity is required.

A variation of this in-situ lift-out process involves "backside milling" of the lift-out sample. This variation was developed in response to the problem known as the "shower curtain" effect, in which non-uniform high-density materials on the surface of an integrated circuit produce a non-planar face on the lift-out sample after final thinning for TEM preparation. These non-planar surfaces have vertical ridges, parallel to the ion beam direction, that result from slower ion milling rates of denser materials near the top of the sample, where the top is defined as the edge closest to the ion beam source. Such non-uniform layers are quite common in integrated circuits, such as copper or aluminum interconnect traces and tungsten contacts. A planar surface on the lift-out sample in the area thinned for TEM inspection is important for TEM techniques such as electron holography. Backside milling involves inverting the sample before final thinning, so that high density materials in or near the active layer of the integrated circuit no longer impact the result of ion milling.

The process of in-situ lift-out can be simplified into three successive steps. The first is the excision of the sample using focused ion-beam milling and extraction of the sample from its trench. The second is the "holder-attach" step, during which the sample is translated on the probe-tip point to the TEM sample holder. Then it is attached to the TEM sample holder (typically with ion beam-induced metal deposition) and later detached from the probe-tip point. The third and final step is the thinning of the sample into an electron-transparent thin section using focused ion beam milling.

A significant portion of the total time involved in completing a TEM sample with in-situ lift-out is spent during the holder-attach step. The relative amount of time involved depends on the amount of time required to mechanically isolate the lift-out sample from the initial bulk sample (ion beam milling rate), but will vary between 30% to 60% of the total time for TEM sample preparation. The elimination of the holder-attach step provides several key revenue and resource-related advantages, due to the elimination of the need to transfer and attach the TEM sample to the TEM sample holder.

For example, without the holder-attach step the semiconductor wafer could be returned to a process flow immediately after lift-out. Thinning of the sample can be performed later in an off-line FIB. This reduces the load on the critical in-line (clean room) FIB, which makes lift-out for process control more practical, and reduces the level of expertise required by process engineers who operate the in-line FIB.

In order to eliminate the holder-attach step, the probe-tip point with the sample attached can be directly joined to the material that will form the TEM sample holder by a suitable method that will preserve the attachment between the lift-out sample and probe-tip point, and prevent the probe-tip point and the sample from separating from the sample holder during storage or inspection in the TEM. The assembly should not interfere with the normal operation of the TEM or other intended analytical instrument, and should survive well in the internal environment of the TEM, or other intended analytical instrument. These suitable methods include, but are not limited to, mechanical deformation of the sample holder material or probe-tip point material, or both; electrical or thermal bonding (such as, electrical welding) of the probe-tip point to the TEM sample holder material; bonding the probe-tip point to this material with a suitable glue or adhesive; bonding the probe-tip point to the TEM sample holder material with a CVD or evaporated material; or other suitable means. This direct attachment of the probe-tip point with the sample attached to it, to the TEM sample holder can be performed inside or outside the vacuum chamber of the FIB or other analytical instrument.

SUMMARY

The preferred embodiment includes a coupon for preparing a TEM sample holder. The coupon comprises a sheet of material, preferably copper or molybdenum, and its surface may be planar or have corrugated structure. The sheet includes a TEM sample holder form, and there is at least one section of the sheet connecting the TEM sample holder form to other portions of the sheet.

In another preferred embodiment, a TEM sample holder form comprises a sheet of material that has a C-shaped hole. The C-shaped hole defines the outer circumference of a ring, and the mouth of the C-shaped hole defines a land of material. The land connects the ring to the sheet, and there is a path across the sheet connecting the C-shaped hole to the edge of the sheet.

The TEM sample holder comprises a ring, and the ring has a circumferential gap. The circumferential gap is formed by cutting the circumferential gap from a TEM sample holder form by pressing this form between two dies. The TEM sample holder may further comprise one or more probe-tip points embedded in the ring, where every probe-tip point further includes an attached sample. Probe-tip points may be embedded in the ring by applying pressure to the ring and to one or more tip ends, so as to cause plastic flow of the ring material around the shank, or they can be attached to the TEM sample holder using adhesives, or by electrical or thermal welding techniques.

In another preferred embodiment, the TEM sample holder comprises a rectangular or any other geometrical shape, which can be used for holding one or more probe-tip points, every one of which comprises an attached sample.

A method for preparing a sample for examination in a TEM comprises the steps of attaching a sample to the tip of a probe; joining the probe-tip point to a TEM sample holder; and forming a TEM sample holder from the probe-tip point and the TEM coupon.

The preferred embodiment further includes a press for cutting a TEM sample holder from a TEM coupon and joining a probe-tip point with an attached sample to the TEM sample holder. The press includes: an outer die; an inner die situated inside the outer die; a former rod opposing the inner and outer dies; and, a shear punch situated coaxially with the former rod. A hold-down spring biases the former rod toward the inner die. A trigger or other mechanism responsive to the contact of the former rod and the inner die, and an actuator responsive to the trigger, drive the shear punch toward the inner and outer dies. This press can be located either inside or outside the vacuum chamber of the FIB or other analytical instrument.

DRAWINGS

DESCRIPTION

The preferred embodiment includes a novel method and apparatus for adjoining a probe tip with attached sample to a TEM sample holder that replaces the holder-attach step of the conventional method. In the preferred embodiment, this mechanical process is performed outside the vacuum chamber, although it could be performed inside the FIB chamber as well. In the preferred embodiment, the first step of the in-situ lift-out procedure (the excision of the sample) is completed in the FIB, and the probe-tip point with the sample attached is then removed from the FIB chamber. This removal can be accomplished by a number of means, including but not limited to, removal of the probe tip and attached sample through the sample door of a FIB equipped with a door, translation of the probe tip and attached sample through a vacuum airlock on the nano-manipulator device, or the translation of the probe-tip point and attached sample in a cassette that passes through a vacuum airlock on the FIB chamber. All but the first means listed do not require that the FIB vacuum chamber be vented to atmosphere, which offers cycle time reduction and long-term equipment reliability advantages.

The Coupon

Figure 1:
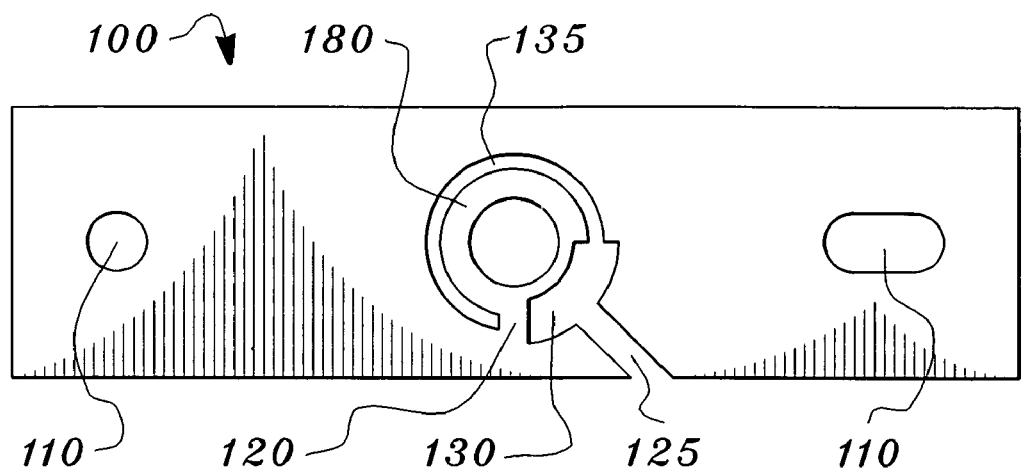
FIG. 1 is a plan view of the TEM coupon of the preferred embodiment, where the sample holder has a ring shape and one probe tip is intended for use.

In the preferred embodiment, the probe-tip point (160) of a nano-manipulator probe (150) is attached to a TEM coupon (100) by a combined mechanical forming and cutting operation. As shown in FIG. 1, the TEM coupon (100) is a sheet of material of approximately the same thickness as the final sample holder (170). The TEM coupon (100) contains the shape of the final sample holder (170) (the "TEM pre-form"), although this pre-form has not yet been completely mechanically isolated. Most of the final shape of the typical 3 mm TEM sample holder (170) can be created in the sheet in advance, as consumable coupons (100). The pre-form is still attached to the coupon (100) with tabs, lands, or other sections of the sample holder material (120). The pre-form has a ring (180) that will be a part of the final TEM sample holder (170). The ring (180) is thus defined by a C-shaped hole (135) in the coupon (100). The mouth of the C-shaped hole (135) is the attaching land (120). Other enclosing shapes, such as rectangles, may also be used.

Figure 2:
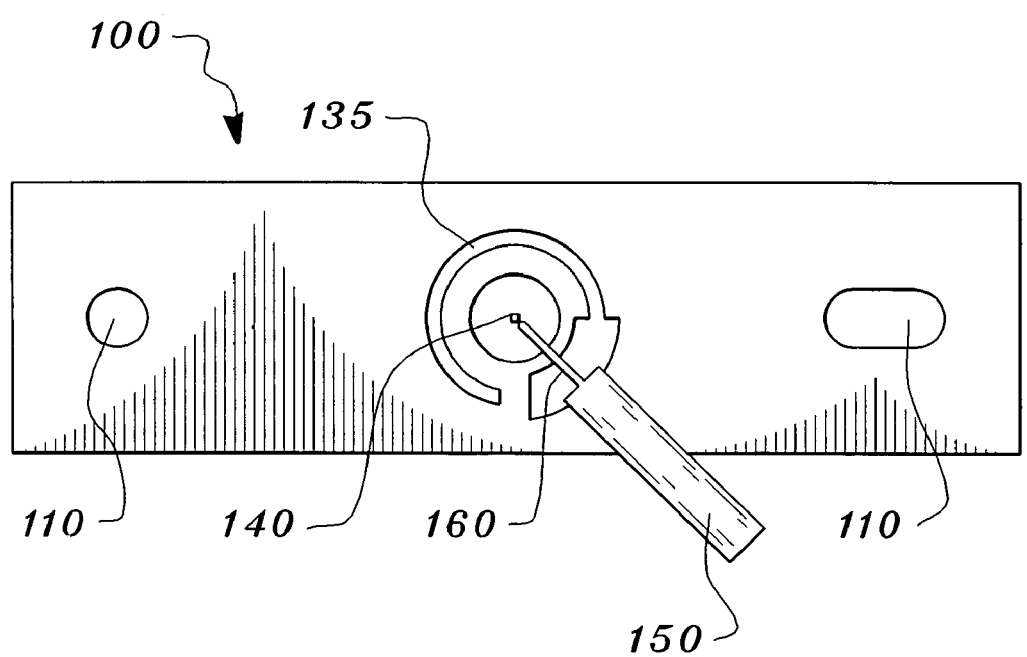
FIG. 2 is a plan view of the TEM coupon of FIG. 1, showing a probe tip positioned across it before embedding and cutting.

The holder material is preferably soft copper, but may also be molybdenum, aluminum, gold, silver, nickel or beryllium, if appropriate to the application. The coupon (100) orients the sample holder form (170) and holds it in place during the mechanical steps of the isolation process, described below. FIG. 2 shows a nano-manipulator probe tip (150) placed across the coupon (100). The probe (150) has a probe-tip point (160) that holds a sample (140) for analysis. Typically, the probe-tip point (160) is a fine tungsten needle.

Figure 7:
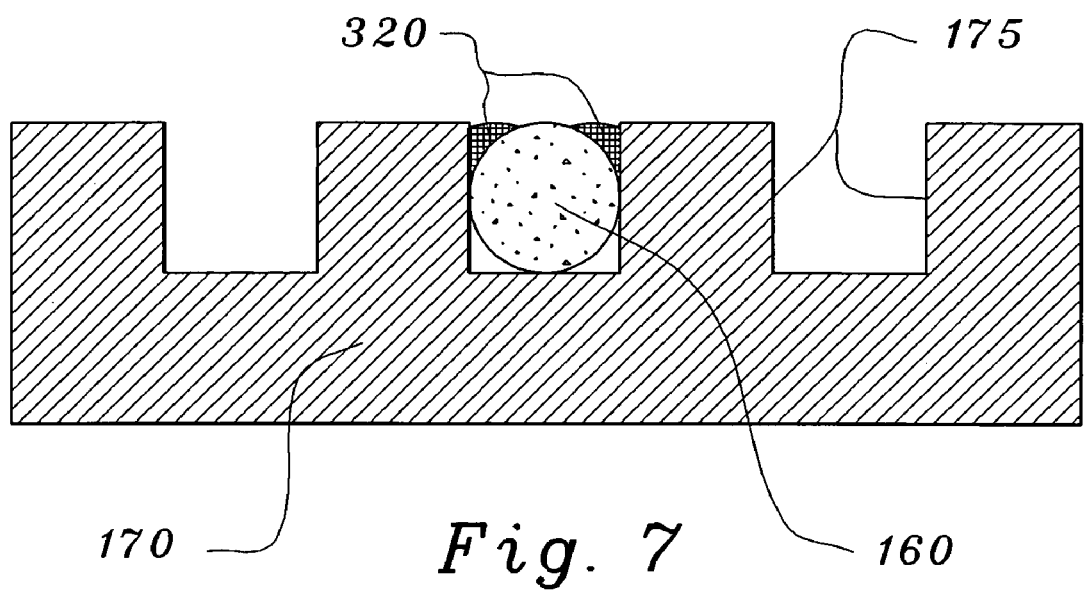
FIG. 7 is a cross-sectional view of a probe-tip point attached to a TEM corrugated coupon via electrical or thermal bonding.
Figure 17:
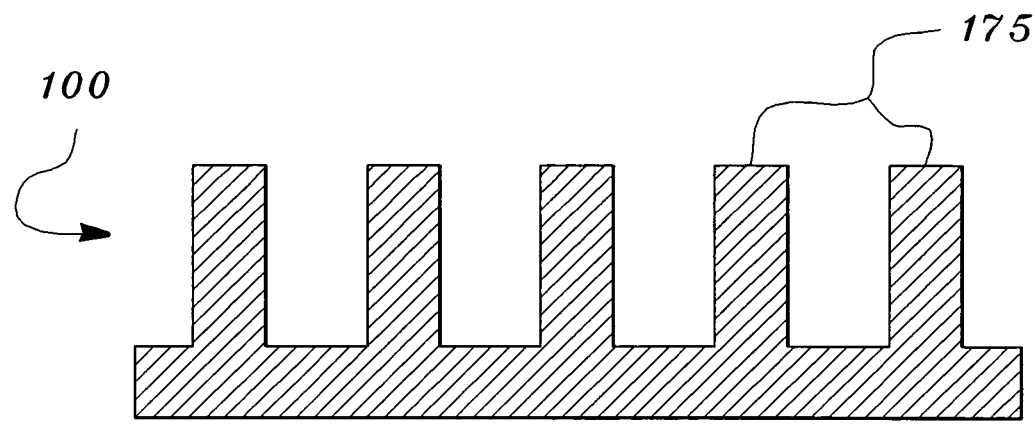
FIG. 17 is a transverse view of a corrugated TEM coupon.
Figure 18:
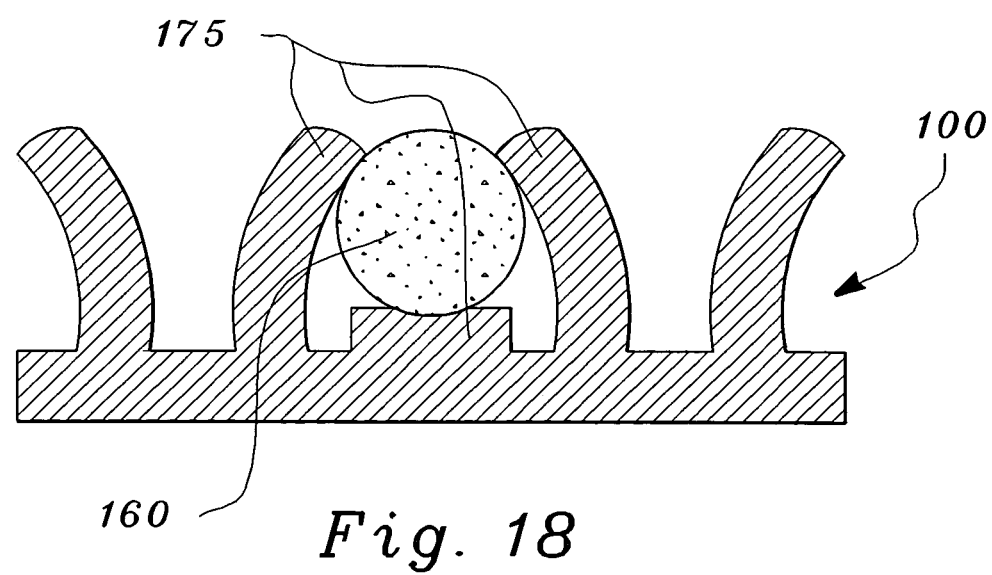
FIG. 18 is a transverse view of a probe-tip point, embedded in a corrugated TEM coupon.

The TEM coupon (100) may also be fabricated from a material harder than copper, such as molybdenum or it may have a surface structure that facilitates the mechanical embedding of the probe-tip point (160) in the coupon material. A good example is a surface structure with corrugations (175) that have a period approximately the same or less than the probe-tip point (160) diameter. FIGS. 7 and 17 show cross-sections of a corrugated structure. In FIG. 7, the corrugation period is about half the diameter of the probe-tip point (160). The corrugations (175) may be periodic, such as continuous rows or ridges roughly aligned in the direction of the probe-tip point, rows of individual posts, or non-periodic free-form elevations. These structures can be easily deformed to lock the probe-tip point (160) in place.

Figure 19:
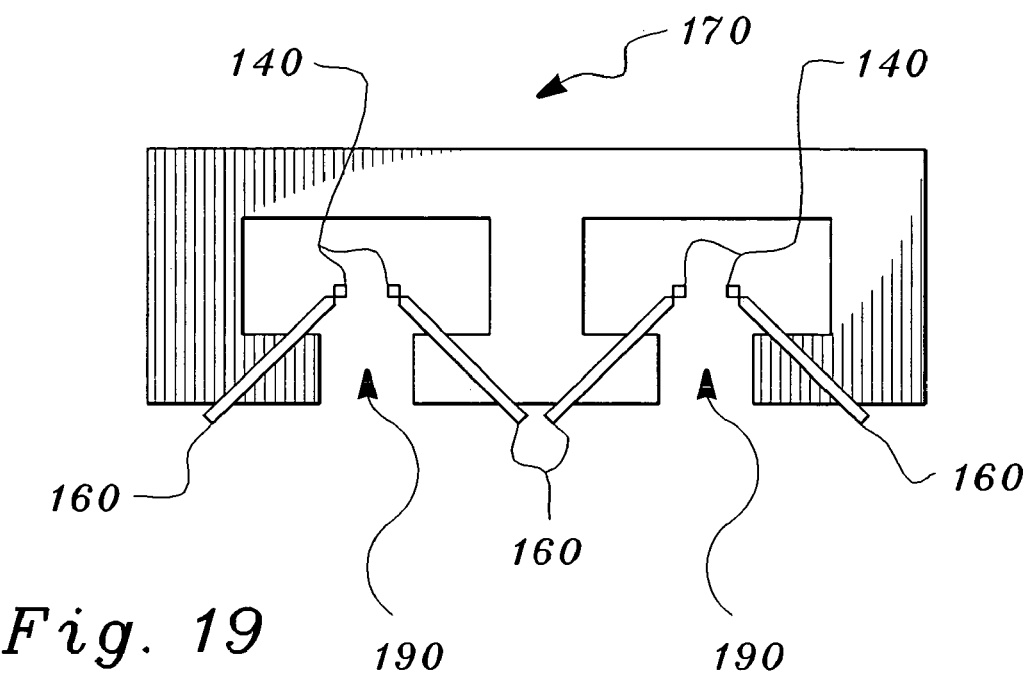
FIG. 19 is a plan view of the TEM coupon of the preferred embodiment, where the sample holder has a rectangular shape and four probe tips are intended for use, with an opening allowing the sample top surface FIB ion milling.
Figure 20:
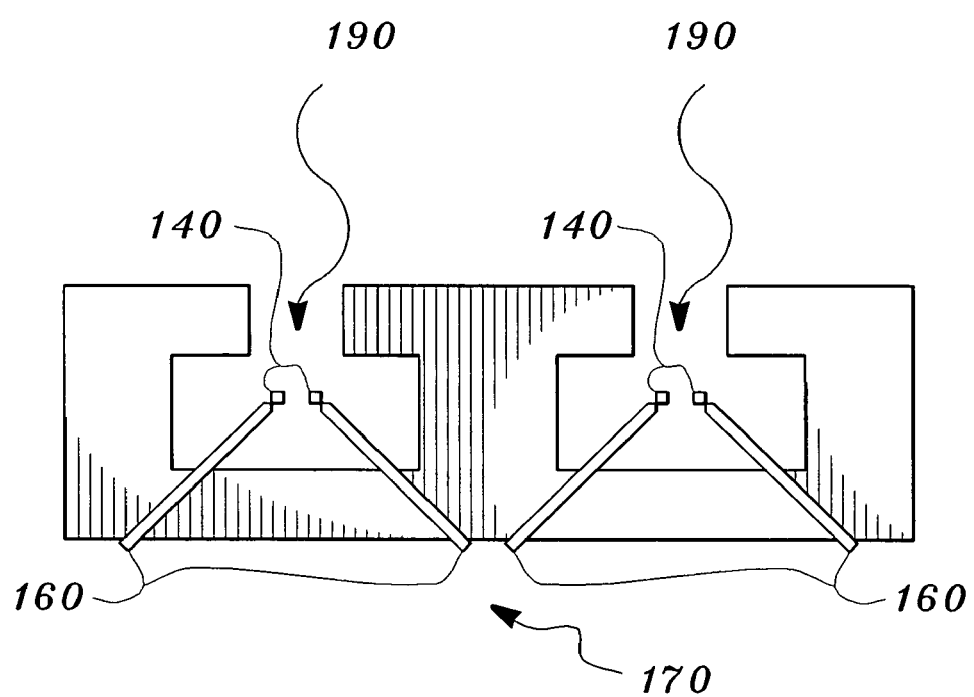
FIG. 20 is a plan view of the TEM coupon of the preferred embodiment, where the sample holder has a rectangular shape and four probe tips are intended for use, with an opening allowing backside FIB ion milling of the bottom surface of lift-out samples.

The remaining tabs, or lands (120) of the coupon material, which connect the partially formed TEM sample holder (170) to the coupon (100), are severed during the combined mechanical forming and cutting operation, described below. The TEM sample holder (170) is preferably produced in the shape of a ring (180) with a circumferential gap (190) to enable later FIB ion milling of either top or bottom surface of the sample (140) in the plane of the TEM sample holder (170), thus producing an electron-transparent thin section that would be approximately parallel to the plane of the TEM sample holder (170). Other shapes that allow for a circumferential gap (190) in the ring (180) of the formed TEM sample holder (170) may also be used. FIGS. 19 and 20, for example, shows a TEM sample holder (170) having two gaps (190), where the shape of the TEM sample holder (170) is rectangular.

Figure 4:
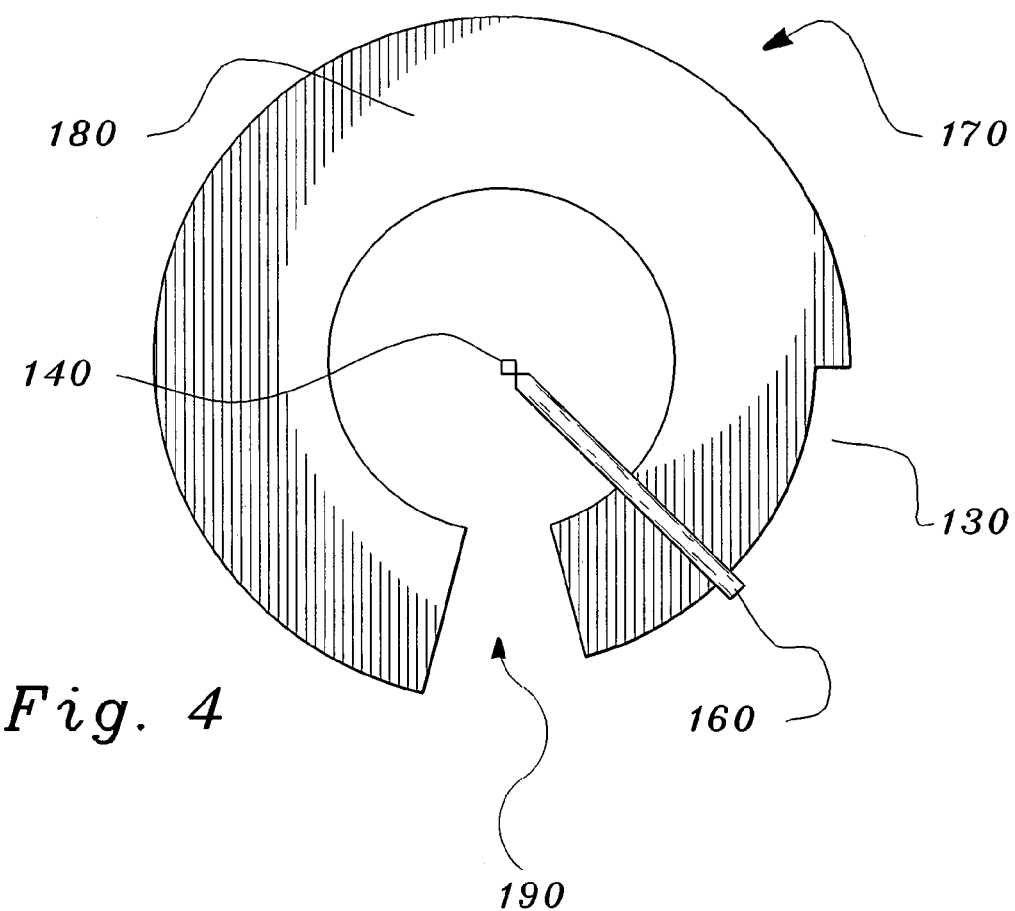
FIG. 4 is a plan view of the TEM sample holder and probe-tip combination, formed from the TEM coupon of FIG. 1, with a ring opening allowing FIB ion milling of the top surface of the lift-out sample.
Figure 5:
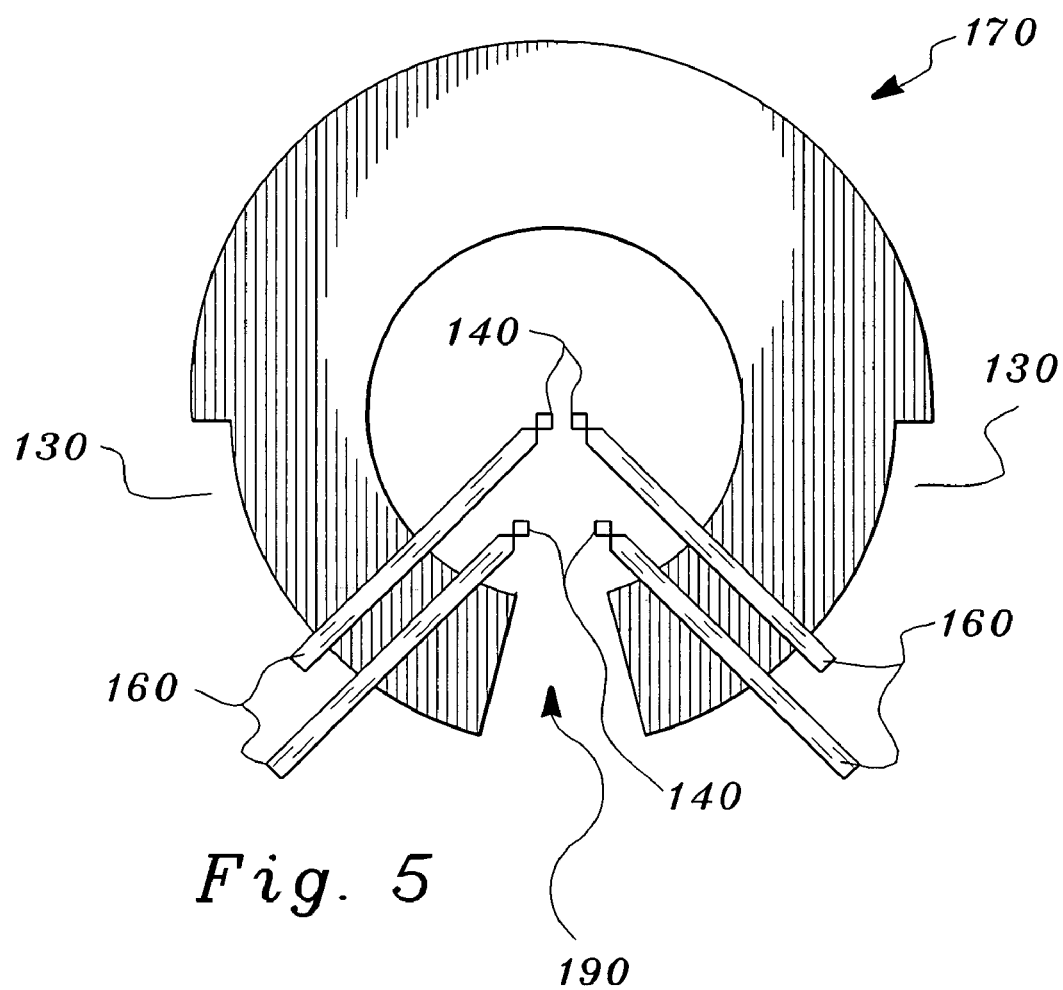
FIG. 5 is a plan view of the TEM sample holder and the four probe-tip combination, formed from the TEM coupon of FIG. 2, with a ring opening allowing FIB ion milling of the top surface of the lift-out sample.
Figure 16:
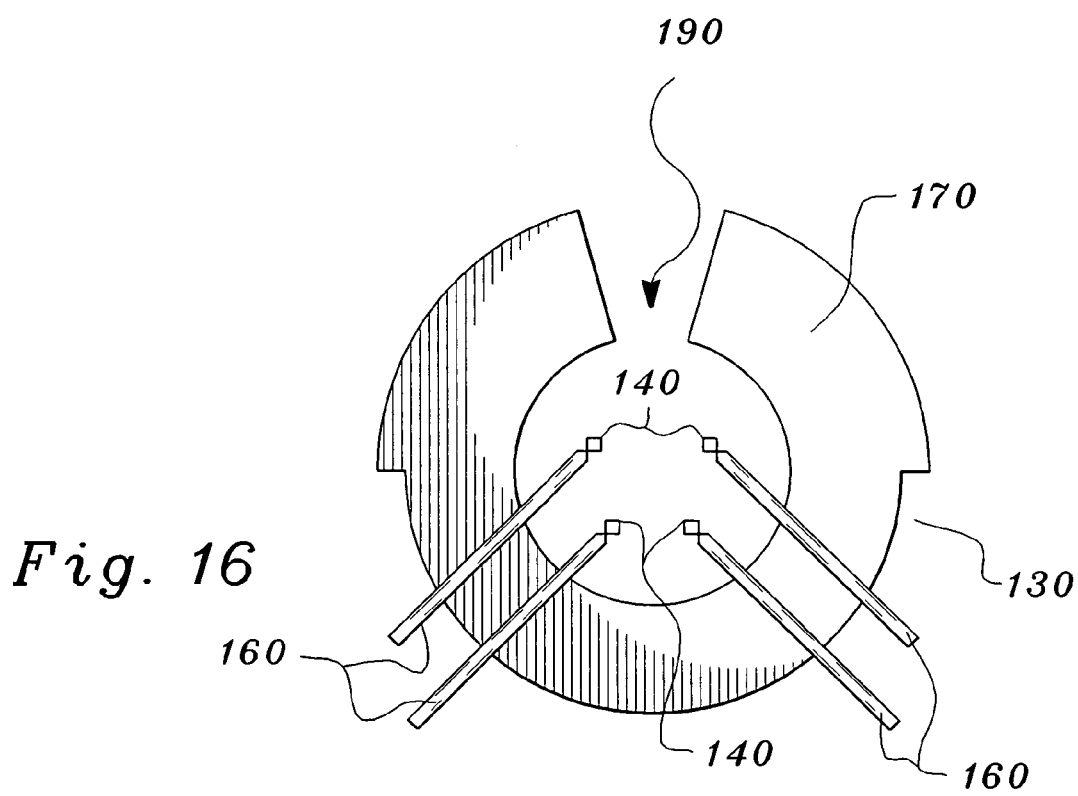
FIG. 16 is a plan view of the TEM sample holder and four probe-tip points combination shown in FIG. 5, with the ring opening made for the backside milling.

FIGS. 4, 5, and 19 show TEM sample holders (170) with probe-tip points (160) mounted for top-side ion milling of samples (140). FIGS. 16 and 20 show TEM sample holders (170) with probe-tip points (160) mounted for back-side milling of samples (140).

Methods of Forming the TEM Sample Holder

The probe-tip point (160) with the sample (140) attached can be joined to the material that will form the TEM sample holder (170), so as to preserve the attachment between the sample (140) and the probe-tip point (160), and prevent the probe-tip point (160) and sample (140) from separating from the TEM sample holder (170) during transportation, storage or inspection in the TEM. The assembly should not interfere with the normal operation of the TEM, or other intended analytical instrument, and should survive well in the internal environment of the TEM, or other intended analytical instrument.

Figure 6:
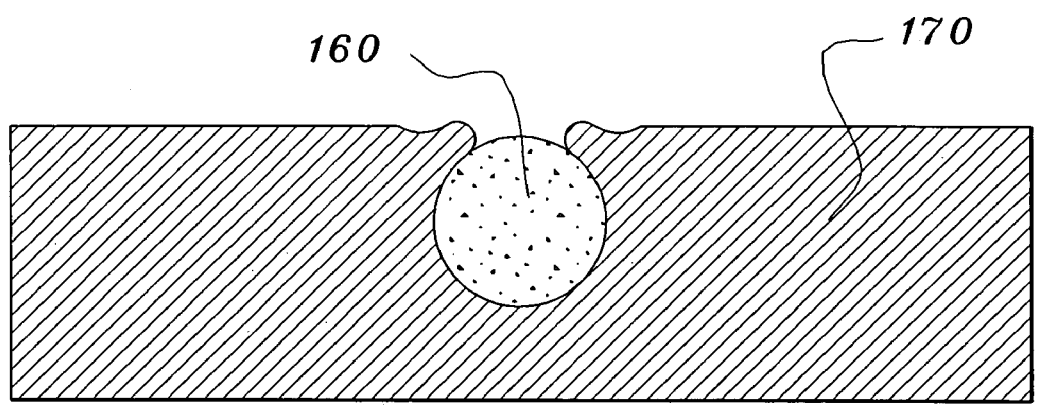
FIG. 6 is a cross-sectional view of a probe-tip point embedded in a TEM coupon.
Figure 8:
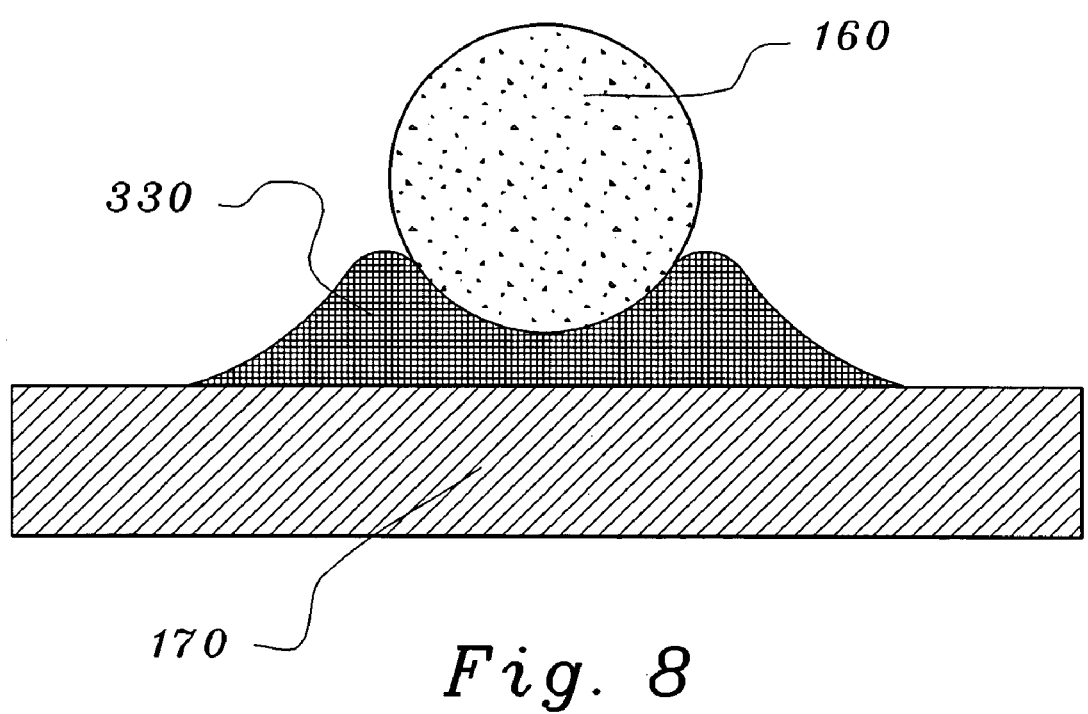
FIG. 8 is a cross-sectional view of a probe-tip point attached to a TEM sample holder using adhesive.
Figures 9, 10:
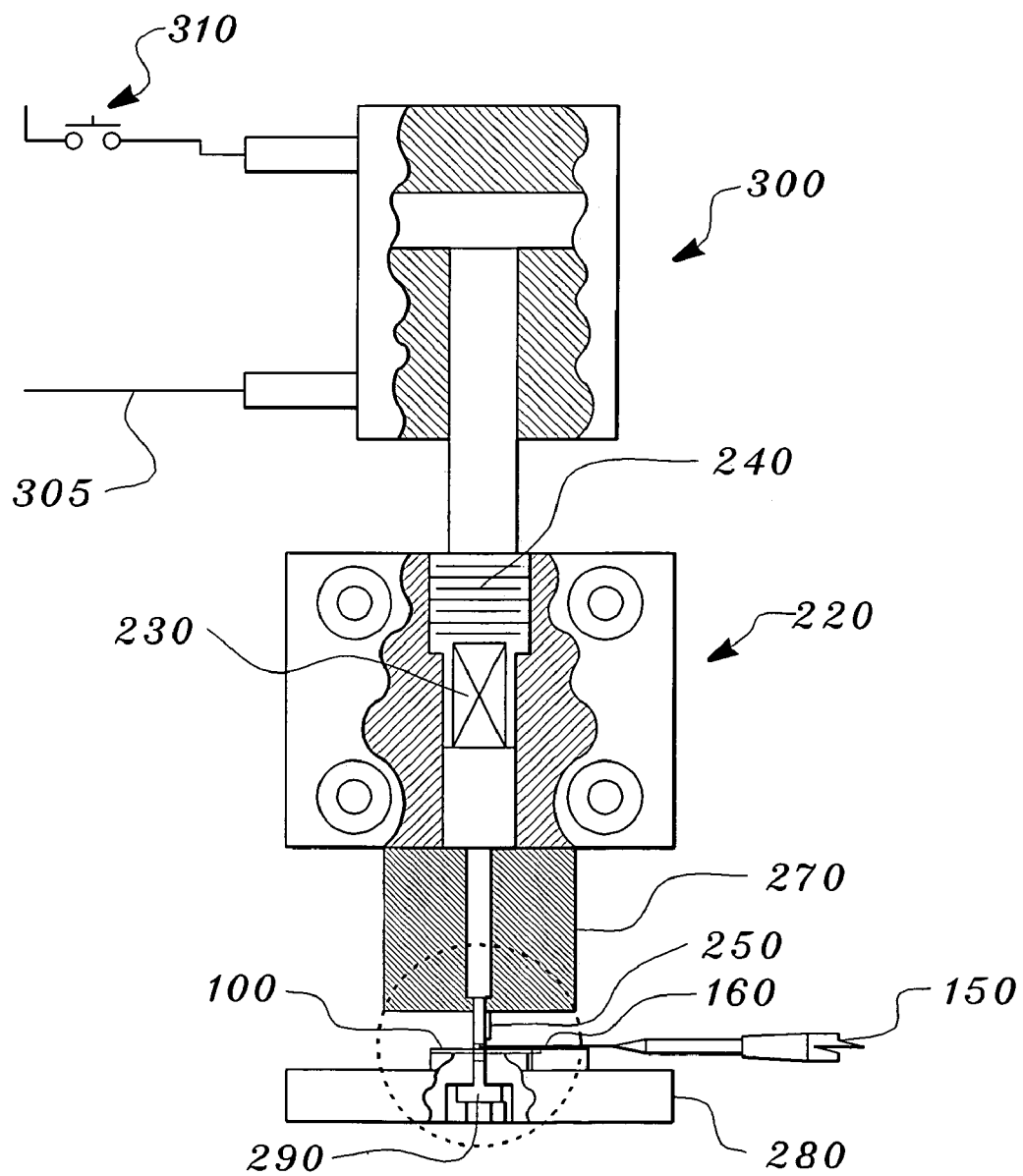
FIG. 9 is a cross-sectional view of a probe-tip point bonded to the TEM sample holder material with a CVD or evaporated material.
FIG. 10 is a partial cross-sectional view of the press and the shear punch of the preferred embodiment.

FIGS. 6–9 and 18 show methods for joining the probe-tip point (160) to the TEM coupon (100). FIG. 6 is a cut-away view of mechanical deformation of the material of the coupon (100) or probe-tip point (160), or both. FIG. 7 depicts electrical or thermal bonding (320), such as welding, of the probe-tip point (160) to the coupon (100). FIG. 7 also shows corrugations (175) in the TEM sample holder material; in this case the corrugation period is about the same as the diameter of the probe-tip point (160). FIG. 8 shows bonding the probe-tip point (160) to the TEM sample holder (170) material with a suitable glue or adhesive (330). FIG. 9 shows bonding the probe-tip point (160) to the TEM sample holder (170) material with a CVD or evaporated material (340).

Once the TEM sample holder (170) with one or more probe-tip points (160) with samples (140) attached to it has been created, it can be returned to the FIB for the final thinning operation, during which the desired portion of the lift-out sample (140) or samples is thinned to electron transparency (typically 50–250 nm). This final thinning can be performed in an off-line FIB to maximize throughput of the in-line FIB and to take advantage of the efficiency, expertise and dedicated resources of the off-line FIB lab that can be located outside the clean room. However, if the apparatus for attaching a sample to a TEM sample holder is located inside the FIB, the final thinning operation can be performed immediately.

In an alternative method, the final thinning step can be performed in the FIB after the lift-out step and before the probe-tip point (160) with the sample (140) attached is removed from the FIB for attachment to the TEM sample holder outside the FIB. In this method, it is not required to return the mechanically formed TEM sample holder (170) with the sample (140) attached, to the FIB for final thinning. However, the final thinning process requires the additional time in the initial FIB. In this method, the probe-tip point (160) with the sample (140) attached is translated to a suitable location in the FIB, and the ion beam in the FIB is then used to perform the final thinning step. Then, the probe-tip point (160) with the thinned sample (140) attached is removed from the FIB and attached to the TEM sample holder (170) using the mechanical forming and cutting process described above. It is recommended, but not required, to stabilize the probe-tip point (160) mechanically to reduce any vibration in the probe-tip point (160) relative to the FIB chamber to an acceptable level, or to reduce any mechanical drift of the probe-tip point (160) relative to the FIB chamber. The probe-tip point (160) with the sample (140) attached can be mechanically stabilized by making mechanical contact between the probe-tip point (160) and a suitably stable surface in the FIB, or between the sample (140) and a suitable surface or object in the FIB. For example, the edge or a corner of a mechanical structure attached to the FIB stage, and the probe-tip point (160) can be brought together into mechanical contact. Or, the bottom edge of the sample (140) can be brought into mechanical contact with the surface of the sample stage or any stable mechanical object attached to the sample stage (e.g., the surface of the wafer). The stable object can be rigid, or can be deformable by plastic or elastic deformation, to accept the shape of the probe-tip point (160) or lift-out sample (140) and further dampen any relative mechanical vibration in the probe-tip point (160).

In another alternative method, the final thinning step can be performed in the FIB after the lift-out step and before the probe-tip point (160) with sample (140) attached is joined to the TEM sample holder inside the FIB vacuum chamber. In this method, the probe-tip point (160) with the lift-out sample (140) attached is translated to a suitable location in the FIB, and the ion beam in the FIB is then used to perform the final thinning step. Then, the probe-tip point (160) with the thinned sample (140) can be attached to the TEM sample holder (170) inside the FIB vacuum chamber using the mechanical forming and cutting process described above. In this method, the apparatus for attaching a sample to a TEM sample holder is located inside the same FIB vacuum chamber. Hence, the in-situ lift-out, the attachment of a probe-tip point with a sample attached to it to a TEM sample holder, and the final thinning operation can be performed as steps of one process inside the FIB vacuum chamber.

Sample Holder Forming Apparatus

FIGS. 1 and 2 show a TEM coupon (100), as described above. The land (120) that connects the sample holder portion (170) of the coupon (100) to the rest of the coupon (100) will be severed to form the TEM sample holder (170) during the cutting and forming operation. The thickness of the coupon (100) is determined by the thickness required to embed and mechanically lock the probe-tip point (160) in the coupon (100) material and still provide for sufficient mechanical strength of the final sample holder (170) to prevent unwanted folding or separation of the TEM sample holder (170) at the probe-tip point (160) embedding location. For example, for the case of a 125 µm (0.005") diameter tungsten probe-tip point (160), a thickness of 250–500 µm (0.010"–0.020") of copper is appropriate for the coupon (100). Both the sample holder (170) material and the surrounding coupon (100) material are slightly recessed in a probe-tip point cut-off zone (130) to allow space for the cutting surfaces to cut the probe-tip point (160) without leaving any portion of the severed probe-tip point (160) extending beyond the 3 mm outside diameter of a standard TEM sample holder (170) or extending beyond the outside border of a standard TEM sample holder (170) of any other suitable shape.

Figure 3:
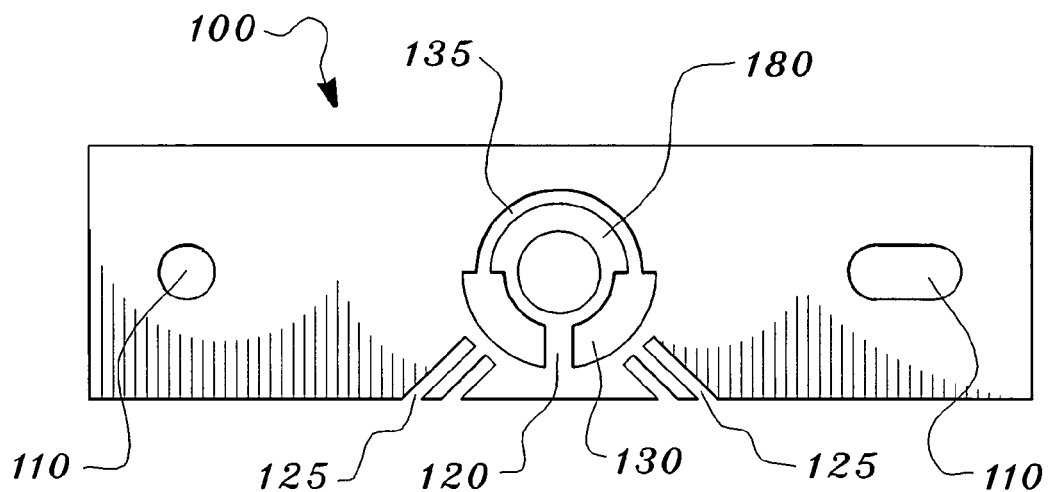
FIG. 3 is a plan view of the TEM coupon of an alternate embodiment, where the sample holder has a ring shape and four probe tips are intended for use.

Alignment holes (110) are included to permit alignment of the coupon (100) in the mechanical apparatus that performs the cutting and forming operation. In the case of a C-shaped TEM sample holder (170), the probe-tip point clearance slot (125) (FIG. 3) is a straight slot through the coupon (100), radiating outward from the center of the TEM sample holder (170) beyond the outer diameter of the TEM sample holder (170), that provides clearance for the probe-tip point (160) to permit alignment of the probe-tip point (160) along the surface of the TEM sample holder (170) before the cutting and forming operation.

During the cutting and forming operation, a TEM sample holder (170) is cut from the coupon (100) (FIG. 4). As discussed above, the TEM sample holder (170) can be produced in a C-shape form, or other shape having a circumferential gap (190) to enable later FIB ion milling of the lift-out sample in the plane of the TEM sample holder (170) to produce an electron-transparent thin section approximately parallel to the TEM sample holder (170) plane, or in any other shape allowing the same process. For later milling of the top surface of a sample (140), the gap (190) can be cut from the form at the mouth of the C-shaped hole (135), defined by the land (120) connecting the form to the coupon (100). For later milling of the bottom surface of a sample (140), the gap can be cut from the form at a location approximately opposite the mouth of the hole (135).

During the cutting and forming operation, the harder tungsten probe-tip point (160) is pressed into the softer material of the TEM sample holder (170), and the portion of the probe-tip point (160), extending outside the outer diameter of the 3 mm TEM sample holder shape (170), is cut off. The TEM sample holder (170) material is induced to plastically deform so that the copper material mechanically surrounds the probe-tip point (160) to lock it in place (FIG. 6).

FIGS. 10–13 show a typical process for the cutting and forming operation. The operator places the TEM coupon (100) on the outer die (280) (this operation can be performed by hand, if this operation is performed outside the FIB, or automatically, if it is performed inside the same FIB vacuum chamber) and aligns every probe-tip point (160) in such a way, that every probe-tip point (160) is aligned with the probe-tip point clearance slot (125), and the sample (140), attached to a probe-tip point (160), is oriented parallel to the plane of the TEM sample holder (170). The inner die (290) and the outer die (280) both support the sample holder (170) and the probe-tip point (160). Once every probe tip is secured, the operator positions by hand or automatically the probe tip or probe tips, TEM coupon (100), and all supporting hardware under the main mounting block (220), and actuates a pneumatic switch (310), causing the main mounting block (220) and attached hardware to travel downward under the action of an actuator (300) located above the main mounting block (220). The actuator (300) is preferably pneumatic, but hydraulic or electrical actuators may also be used. There is also the exhaust line (305) for pneumatic actuators.

Figure 11:
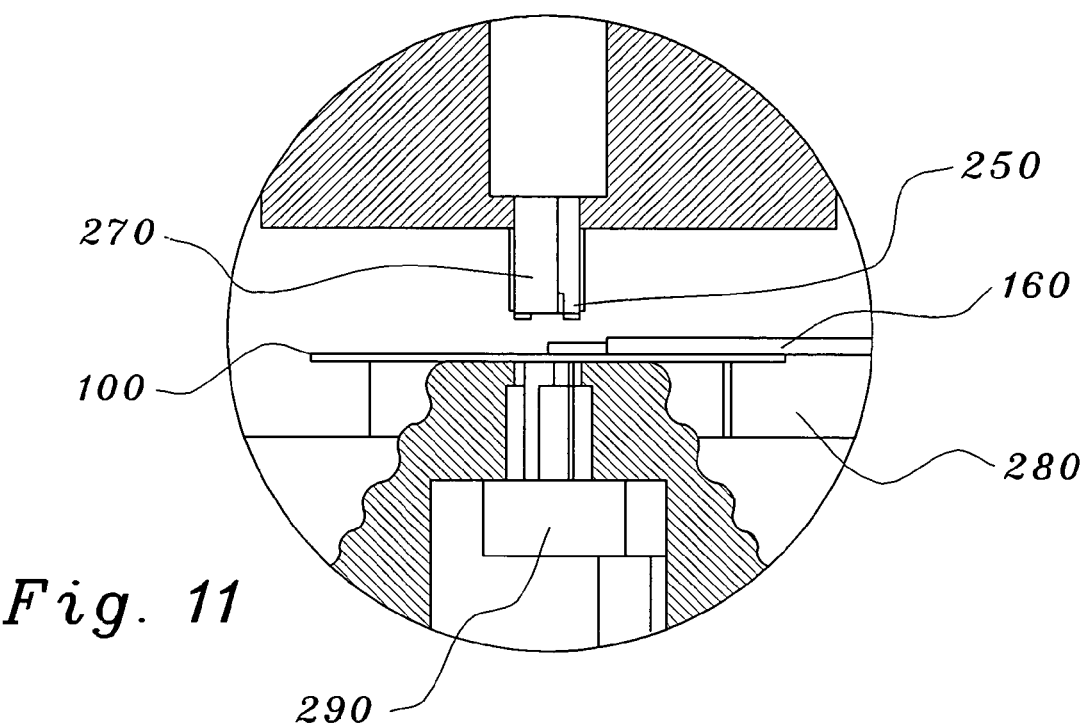
FIG. 11 is an enlarged partial cross-sectional view of the press and the shear punch of FIG. 10.
Figure 12:
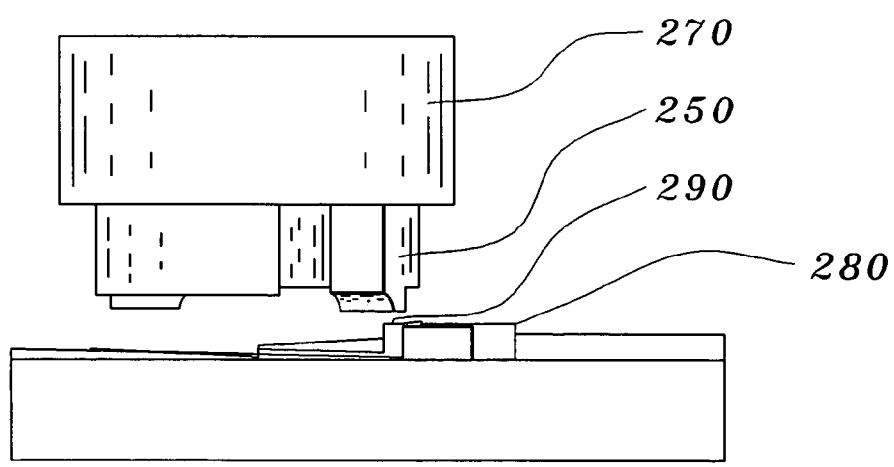
FIG. 12 is a perspective view of the shear punch of FIG. 10 and the inner and outer dies.
Figure 13:
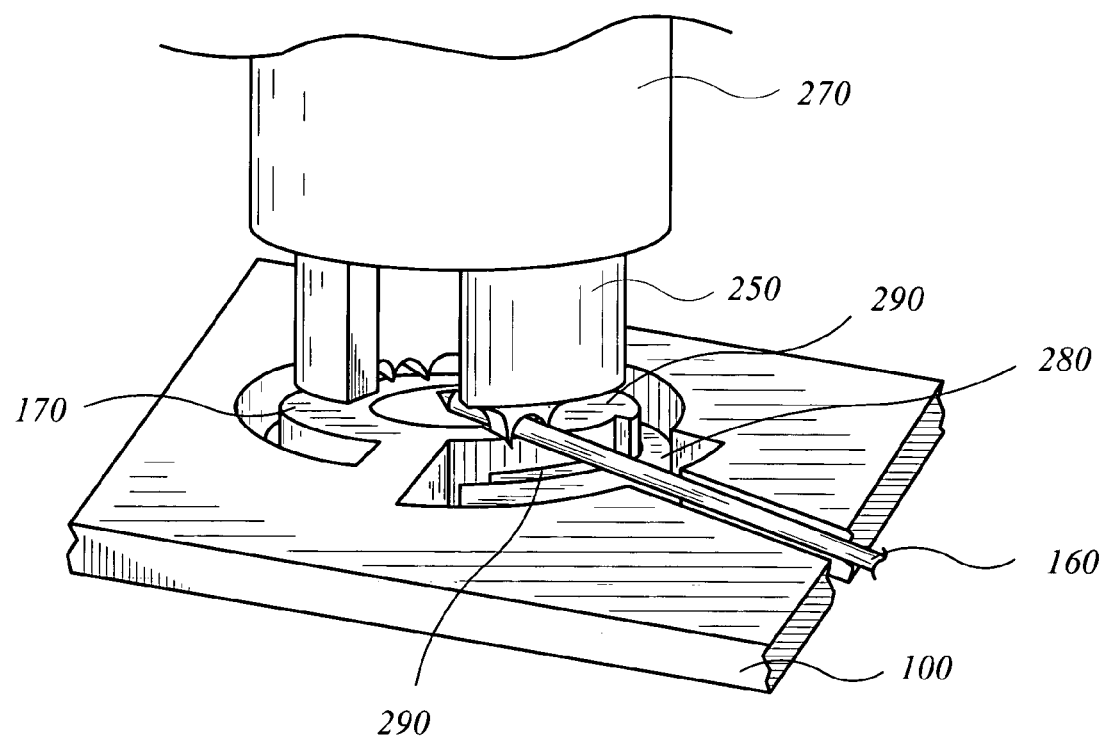
FIG. 13 is a perspective view of the shear punch of FIG. 10, shown engaging a coupon and a probe tip.
Figure 14:
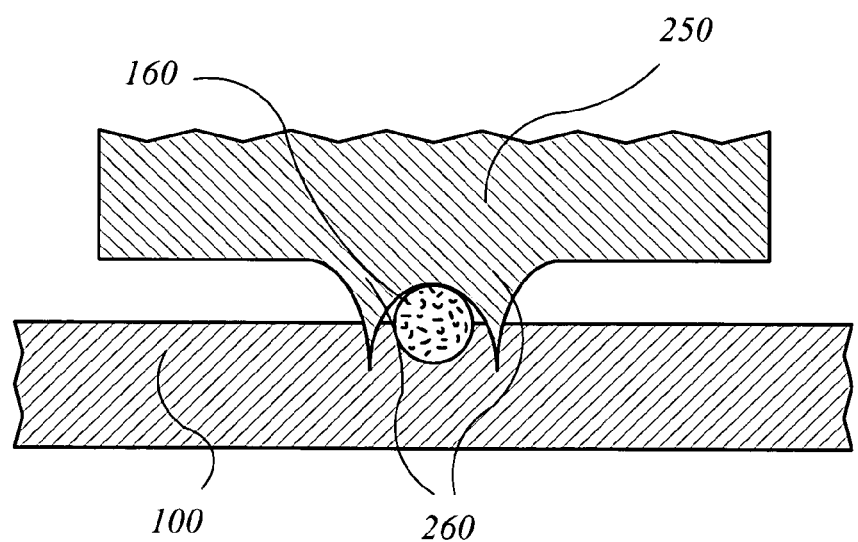
FIG. 14 is a transverse view of the probe-tip point, tip former rod of the preferred embodiment positioned above a probe-tip point, and a TEM sample holder, with the probe-tip point embedded in a TEM sample holder.
Figure 15:
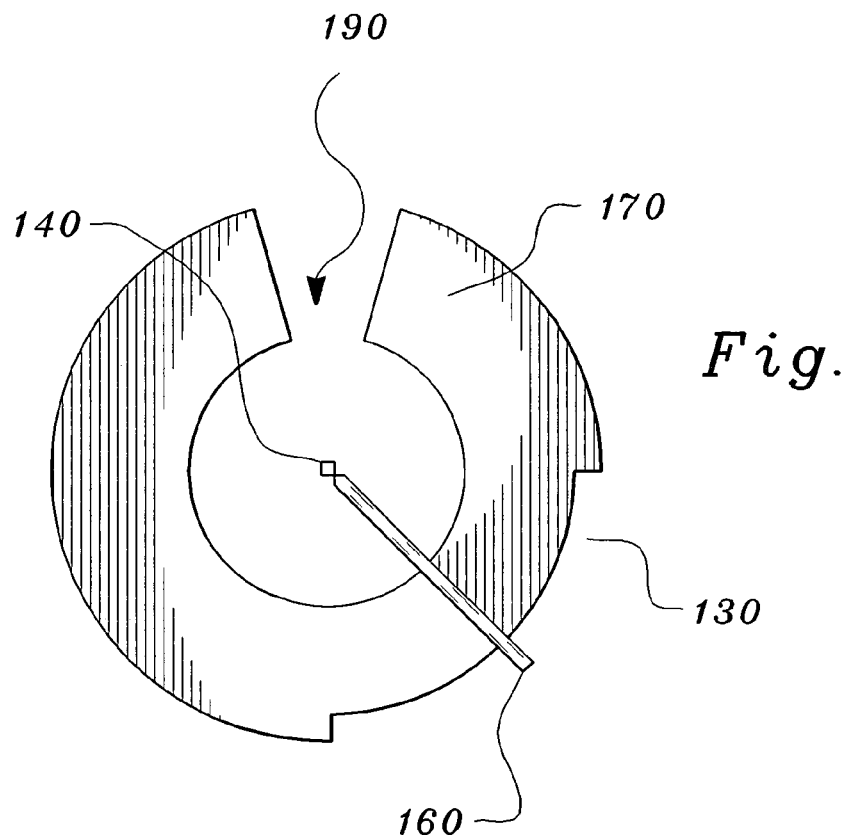
FIG. 15 is a plan view of the TEM sample holder and probe-tip point combination shown in FIG. 4, with the circumferential gap made in the sample holder ring for the backside milling.

FIGS. 11–13 show the forming and cutting operation as the main mounting block (220) moves downwards. The former rod (250) contacts every probe-tip point (160) and presses it down into the TEM sample holder (170) material. This continues until the TEM sample holder and the probe-tip point interface build up enough resistance to overcome the force of the hold down spring (230). The hold down spring (230) force is set with a spring adjustment screw (240) to the desired force to ensure that every probe-tip point (160) is pressed fully into the TEM coupon (100). The former rod (250) includes one or more teeth (260) that flow the holder material around the probe-tip point (160) encasing it as it is pressed down (FIG. 14).

Once resistance to the spring (230) is overcome and the former rod (250) movement is stopped, the shear punch (270) continues its travel downward, using the support of both the inner die (290) and the outer die (280) to shear every probe-tip point (160) at the desired length, sever the tab (120) connecting the TEM sample holder (170) from the rest of the TEM coupon (100) and create the C-shaped opening, or the opening of any other suitable shape, in the holder (170). The operator then releases a pneumatic switch to return the main mounting block (220) and attached hardware to its original position, leaving the TEM sample holder (170) separated from the TEM coupon (100) and containing one or more probe-tip points (160) with the samples (140) attached.

Since those skilled in the art can modify the specific embodiments described above, I intend that the claims be interpreted to cover such modifications and equivalents.

I claim:

1. A coupon for preparing a TEM sample holder, the coupon comprising:
   a sheet of material,
   the sheet comprising a TEM sample holder form; and,
   one or more paths through the sheet connecting the TEM sample holder form to the edge of the sheet.

2. The coupon of claim 1 where the sheet comprises a metal selected from the group consisting of copper, molybdenum, aluminum, gold, silver, nickel and beryllium.

3. The coupon of claim 1 where the sheet has surface corrugations.

4. The coupon of claim 1 where the coupon further comprises alignment holes, for aligning the coupon in a press.

5. The coupon of claim 1 further comprising:
   at least one hole in the coupon defining the outer boundary of a TEM sample holder form; the hole having a mouth;
   the mouth of the hole defining a land of material;
   the land connecting the TEM sample holder form to the sheet; and,
   one or more paths through the sheet connecting the hole to the edge of the sheet.

6. The coupon of claim 5 where the hole has a C-shape.

7. The coupon of claim 5 where the TEM sample holder has a rectangular shape.

8. The coupon of claim 5 where the hole has a rectangular shape.

* * * * *